United States Patent
Abramson et al.

(10) Patent No.: US 7,074,737 B2
(45) Date of Patent: Jul. 11, 2006

(54) ALKYLATION OF TRIPHENYLPHOSPHATE

(75) Inventors: Alan J. Abramson, Mobile, AL (US); Anantha Desikan, Ossining, NY (US); Shuguang Zhang, New Rochelle, NY (US); Zongchao Zhang, Norwood, NJ (US); James Liang, White Plains, NY (US)

(73) Assignee: Supresta U.S. LLC, Ardsley Park, NY (US)

( * ) Notice: Subject to any disclaimer, the term of this patent is extended or adjusted under 35 U.S.C. 154(b) by 0 days.

(21) Appl. No.: 10/744,466

(22) Filed: Dec. 23, 2003

(65) Prior Publication Data

US 2005/0137425 A1   Jun. 23, 2005

(51) Int. Cl.
*B01J 31/00*   (2006.01)
(52) U.S. Cl. .............................. 502/162; 568/17; 568/8; 568/14
(58) Field of Classification Search .................. 568/17, 568/8, 14; 502/162
See application file for complete search history.

(56) References Cited

U.S. PATENT DOCUMENTS

| | | | |
|---|---|---|---|
| 4,912,264 A | 3/1990 | Takeshita et al. | 568/790 |
| 5,254,766 A | 10/1993 | Fujita et al. | 585/467 |
| 5,300,703 A | 4/1994 | Knifton | 568/794 |
| 5,334,775 A | 8/1994 | Gutierrez et al. | 568/791 |
| 6,486,339 B1 | 11/2002 | Desikan et al. | 558/92 |

FOREIGN PATENT DOCUMENTS

| | | | |
|---|---|---|---|
| CA | 967168 | 5/1975 | 260/461 |
| EP | 1028102 | 8/2000 | |
| GB | 1369346 | 10/1974 | |
| JP | 62010029 | 1/1987 | |
| JP | 08-182005 | 7/1996 | |
| WO | 95/13869 | 5/1995 | |
| WO | 00/40527 | 7/2000 | |

*Primary Examiner*—Johann Richter
*Assistant Examiner*—Chukwuma Nwaonicha
(74) *Attorney, Agent, or Firm*—Dilworth & Barrese, LLP

(57) ABSTRACT

A process for the alkylation of triphenylphosphate by reaction of triphenylphosphate with an olefin in the presence of an effective amount of a solid acid catalyst selected from the group consisting of at least one zeolite, heteropolyacid or salt thereof, metal triflate, non-aryl group-containing metal sulfonic acid, metal halide Lewis acid, or compatible mixture of any such catalyst.

8 Claims, 5 Drawing Sheets

ALKYLATION OF TRIPHENYLPHOSPHATE

FIELD OF THE INVENTION

Figure 1:
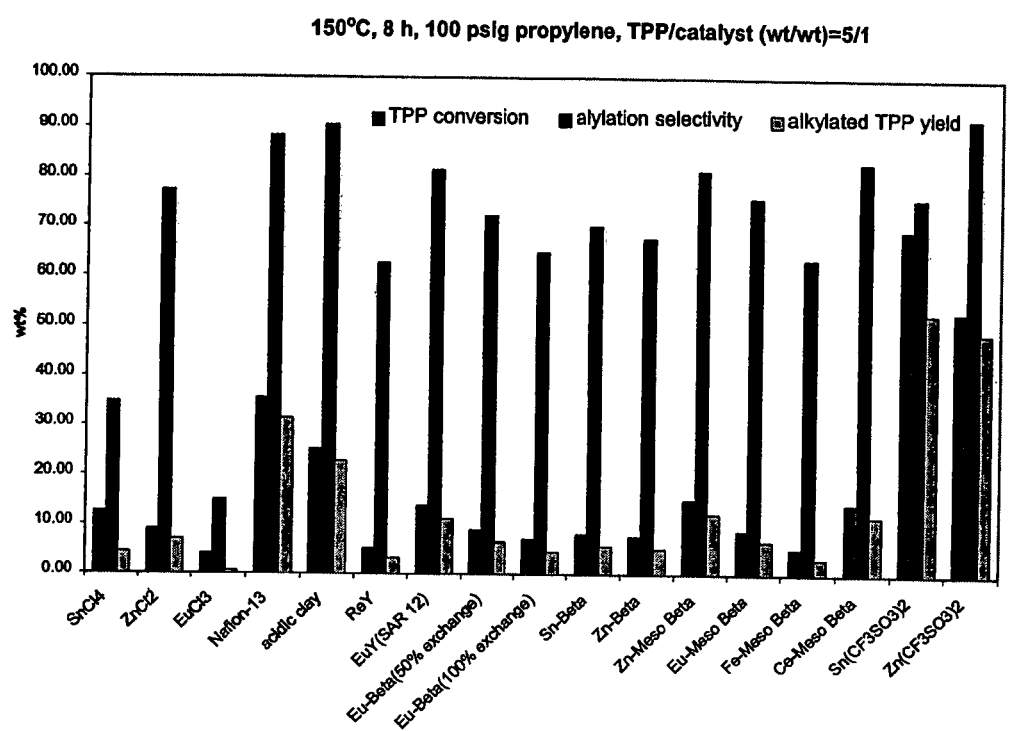

The present invention relates to a catalytic process for the alkylation of triphenylphosphate using certain types of solid acid catalyst. These catalysts may either dissolve in the feed as a homogeneous catalyst or function as a solid heterogeneous catalyst.

BACKGROUND OF THE INVENTION

While the alkylation of aromatic compounds with catalysts, such as the zeolites, is not novel, the alkylation of phosphate aromatic esters, as exemplified by triphenylphosphate is quite distinguishable and poses some unique problems. Even though triphenylphosphate possesses aromatic rings, the high polarity of the phosphate moiety distinguishes this compound from non-polar aromatic compounds. Most importantly, cracking of triphenylphosphate is a serious problem in the presence of an acidic catalyst, whereas such a problem does not exist for aromatic compounds. As a result, the alkylation of phosphate aromatic esters becomes considerably more difficult and requires different catalysts and process conditions as compared to those needed for the alkylation of non-polar aromatic compounds. Many catalysts that work for aromatic alkylation fail to work for triphenylphosphate alkylation.

British Patent No. 1,369,346 describes the alkylation of triphenylphosphate at elevated temperature and pressure employing a catalyst that is an aryloxide of aluminum, zirconium, hafnium, niobium, or tantalum, an aryl sulfonic acid, sulfuric acid, an alumina clay, or an acid-activated silica-alumina clay.

SUMMARY OF THE INVENTION

Triphenylphosphate (TPP) can be alkylated with an olefin, such as propylene, using solid acid catalysts with a high yield of alkylated products being obtained. The distribution of the alkyl group in the products will be preferentially at the para position with the number of alkyl groups per molecule of TPP being dependent on the degree of alkylation, on the reaction temperature and length of the reaction period with a given catalyst. The reaction temperature can range from about 150° C. to about 280° C., but lower temperatures can also be employed when a greater amount of catalyst and a longer reaction period is used.

The present invention relates to the alkylation of TPP by reaction of that molecule with an olefin employing an effective amount of a solid acid catalyst selected from the group consisting of at least one zeolite, heteropolyacid or salts thereof, metal triflate, non-aryl group-containing metal sulfonic acid, metal halide Lewis acid, or compatible mixture of any such catalyst. While such catalysts are well known in the art of catalysis for a variety of reactions, they have not been employed heretofore in the alkylation of TPP.

DETAILED DESCRIPTION OF THE PRESENT INVENTION

The catalyst for use in the process of the present invention is characterized by being a material selected from the group consisting of at least one metal-ion exchanged zeolite, heteropolyacid or salt thereof, metal triflate, non-aryl group-containing metal sulfonic acid, metal halide Lewis acid, or compatible mixture of any such catalyst.

Zeolites are crystalline aluminosilicates generally represented by the formula

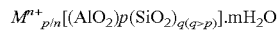

$$M^{n+}_{p/n}[(AlO_2)p(SiO_2)_{q(q>p)}].mH_2O$$

where M is a metal cation of Groups IA, including hydrogen, or IIA of the Periodic Table of the Elements and n is the valency of such metal. Zeolites consist of a network of $SiO_4$ and $AlO_4$ tetrahedra linked together via shared oxygen atoms. Aluminum has a +3 valency, resulting in an excess negative charge on the $AlO_4$ tetrahedra, which can be compensated by cations, such as $H^+$. When M is hydrogen, the materials are Bronsted acidic, when M is, for example, Cs, the materials are basic. Upon heating, Bronsted acidic hydroxyls dehydrate creating coordinately unsaturated Al, which acts as a Lewis acid site. The acid strength, acid site density and Bronsted versus Lewis acidity are determined by the level of framework aluminum. The ratio of silica/alumina can be varied for a given class of zeolites, either by controlled calcination, with or without the presence of steam, optionally followed by extraction of the resulting extra framework aluminum or by chemical treatment employing, for example, ammonium hexafluorosilicate.

As zeolite frameworks are typically negatively charged, the charge balancing cations suitable for use with this invention include monovalent cations, such as $H^+$, $Li^+$ and the like, divalent cations, such as $Mg^{2+}$, $Zn^{2+}$ and the like, and trivalent cations, such as $Ln^{3+}$, $Y^{3+}$, $Fe^{3+}$, $Cr^{3+}$ and the like. The framework composition of the three-dimensional zeolites may contain other elements in addition to Al and Si, such as, for example, P, Ti, Zr, Mn, and the like. Although any zeolite meeting the parameters of this embodiment are suitable for use in the process of the present invention, faujasite (e.g., Y zeolite), Beta zeolite, and Offeretite are particularly well suited for use.

The Si/Al ratio of the zeolites can vary depending on the particular zeolite employed provided that the person in the art understands that a ratio that is too low will result in more by-products and a ratio that is too high will lower the activity of the zeolite. In most cases, the Si/Al ratio of the zeolites is at least 2, up to at least 20, and higher. For example, the Si/Al ratio for Beta zeolite maybe from about 5–75 while that for Y zeolite can be from 2 to about 80.

The present invention is not limited to the use of such zeolites in general, or to a particular zeolite, as materials other than zeolites can be employed in the context of the present invention. Zeolites are, however, a preferred material to be employed and the use of any known or yet to be discovered zeolites is included within the scope of the present invention. Examples of zeolites which can be employed in the context of the present invention include, but are not limited to, zeolite A, Beta zeolite, zeolite X, zeolite Y, zeolite L, zeolite ZK-5, zeolite ZK-4, zeolite ZSM-5, zeolite ZSM-11, zeolite ZSM-12, zeolite ZSM-20, ZSM-35, zeolite ZSM-23, aluminophosphates including but not limited to VPI-5 and the like, and mixtures thereof, and/or zeolitic materials having the following framework structures: AEL, AFO, AHT, BOG, CGF, CGS, CON, DFO, FAU, FER, HEU, AFS, AFY, BEA, BPH, CLO, EMT, FAU, GME, MOR, MFI, and the like.

The metal ions in zeolites can be from a single metal or from multiple metals, with or without other additives. The source of the metal ions can be from any salts containing the metal ions with or without ligands. Mixed metal ions or their complexes with various ligands can be used. Ion exchange can be carried out in the aqueous phase, or in the absence of an aqueous phase, e.g., solid state exchange by physically mixing the solid materials with one or more metal ion containing salts followed by calcination at elevated temperature. The ion exchange level can range from a trace level of metal ions to substantially 100% metal ion level based on the ion exchange capacity of the material. Over exchange to a level about 100% of the ion exchange capacity can also result in active catalysts. It is known that certain noble metal ions, such as $Pt^{2+}$ and $Pd^{2+}$, in zeolites can be reduced by hydrogen at temperatures above 120° C. Even though most metal oxides can be readily reduced by hydrogen at temperatures of about 350° C., the reduction of most transition metal ions in zeolites by hydrogen generally requires much a higher temperature (see "Location, Ligancy and Reducibility of Metal Ions in Zeolites: Co and Pd in NaY", Z. Zhang, and W. M. H. Sachtler, *J. Chem. Soc. Faraday Trans.*, 86 (1990) 2313). This invention relates to a process in which hydrogen is preferably not used. However, for non-reducible metal ions, the use of hydrogen is not harmful to the product yield.

As an example of the forgoing, the acidic proton form ($H^+$) zeolites, such as HZSM-5, H-Mordenite, HBeta, and HY, are known to be active, for example, for the isomerization of unsaturated fatty acids to branched fatty acids. Proton form zeolites containing Group VIII zero valent metals are also active catalysts since the zero valent metals do not affect the overall proton concentrations in zeolites. When positively charged protons are replaced by metal ions, the overall proton concentrations decrease. As isomerization is known to typically take place via protonated carbenium ion mechanism, the concentration and strength of proton acidity are critical for skeletal isomerization activity of proton form zeolites.

Examples of higher valent metals, which can be exchanged on the catalyst for use in the process of this invention, include, but are not limited to: $Li^+$, $Cu^+$, $Rh^+$, $Ir^+$, $Mg^{2+}$, $Ca^{2+}$, $Mn^{2+}$, $Fe^{2+}$, $Co^{2+}$, $Ni^{2+}$, $Cu^{2+}$, $Zn^{2+}$, $Sr^{2+}$, $Mo^{2+}$, $Pd^{2+}$, $Sn^{2+}$, $Ce^{2+}$, $Pt^{2+}$, $Sc^{3+}$, $Cr^{3+}$, $Fe^{3+}$, $Co^{3+}$, $Ga^{3+}$, $Y^{3+}$, $Nb^{3+}$, $Ru^{3+}$, $Rh^{3+}$, $La^{3+}$, $Ln^{3+}$and the rest of the rare earth elements, $Ir^{3+}$, $Bi^{3+}$, $Ti^{4+}$, $Mn^{4+}$, $Zr^{4+}$, $Mo^{4+}$, $Sn^{4+}$, $Ce^{4+}$, $V^{5+}$, $Nb^5+$, $Mo^{6+}$, mixtures thereof and the like.

Another type of solid acid catalyst that is useful in the practice of this invention are the heteropolyacids, as exemplified by the acidic polymolybdates, polytungstates, polyvanadates, polyniobates, and, in general, the acidic polyoxometallates. In such a class of solid acid catalyst, other divalent (e.g., $Cu^{2+}$, $Mn^{2+}$, $Zn^{2+}$, $Co^{2+}$), trivalent (e.g., $Fe^{3+}$, $Ga^{3+}$, $Al^{3+}$, $Co^{3+}Cr^{3+}$), tetravalent (e.g., $Si^{4+}$, $Ge^{4+}$, $Zr^{4+}$, $Ti^{4+}$, $Mn^{4+}$, $Ce^{4+}$), and pentavalent (e.g., $P^{5+}$, $As^{5+}$, $V^{5+}$) ion substitutions can be used to enhance the acid strength to varying degrees.

Another type of solid acid catalyst that is useful in the practice of this invention are the metal triflates, such as tin triflate, zinc triflate, and the rare earth metal triflates.

Another type of solid acid catalyst that is useful in the practice of this invention includes the non-aryl group-containing metal sulfonic acids as exemplified by such polymeric fluorosulfonic acids resins, such as NAFION resin, and metal oxide-supported NAFION resin.

Another type of solid acid catalyst that is useful in the practice of this invention are the metal halide Lewis acidic materials including but are not limited to metal halides such as $AlCl_3$, $GaCl_3$, $SnCl_4$, $ZnCl_2$, $AlF_3$, and the like.

Good selectivity and conversion can be obtained by the process of the present invention if at least part of the alkylation of triphenylphosphate using any of the aforementioned catalysts is performed at a temperature of from about 100° C. and to about 300° C. In another embodiment, the process of the invention is preferably performed at a temperature of from about 150° C. to about 250° C. Since the conversion is also a function of the reaction/contact time, it is preferred that the feedstock is contacted with the catalyst for a period of at least about 10 minutes and reaction times of from about 1 hour to about 8 ours are typical. An even longer period could be used if the process is operated at a lower temperature.

In general, the amount of catalyst employed in the process according to the invention is from about 0.001% to about 20% by weight when the process is carried out in batch or sem-batch process, based on the total reaction mixture. In another embodiment the amount of catalyst used from about 0.5% to about 10%, by weight. In still another embodiment the catalyst amounts are from about 1% to about 5%, by weight.

The processes of the present invention can be performed both in batch and fixed bed continuous embodiments.

When a continuous flow reactor is employed, the weight hour space velocity is from about 0.01 to about 100. Weight hour space velocity is defined as the weight of feed in grams passing over one gram of catalyst per hour.

Additionally, it has been found that by using a catalyst system according to this invention it is possible to reuse the catalyst. In some cases it maybe desired to add fresh catalyst while optionally removing a part of the spent catalyst, and in other cases regeneration of the catalyst may be desired. Regeneration can be effected by various methods know to the skilled artisan. For example, regeneration can be accomplished by utilizing controlled oxidative regeneration and/or by washing with a solvent.

The invention will be illustrated by the nonlimiting Examples that follow.

EXAMPLES

Ion-Exchange Procedure

Two general procedures for ion-exchange have been employed to prepared metal ion exchanged zeolites: aqueous ion-exchange and solid state ion-exchange. Examples of Cu (II) ion exchanged zeolites are given below.

Aqueous Procedure

To conduct aqueous ion-exchange, a calculated amount of metal salt, for example $Cu(NO_3)_2$ for $Cu^{2+}$ exchange, is dissolved in distilled and deionized water. Then certain amount of $NH_4^+$ form zeolite is added. The weight ratio of the water to the zeolite is about 12. The amount of metal salt added depends on how much $NH_4^+$ cations in the zeolite needs to be exchanged. For example, if 4000 g of zeolite contains 1 mol $NH_4^+$ and an exchange of 20% is desired, then 0.1 mol of $Cu^{2+}$ is needed since 1 mol $Cu^{2+}$ can replace 2 mol of $NH_4^+$. Therefore, 0.1 Mol of $Cu(NO_3)_2$ will be added to 48 L water and then 4000 g of the zeolite is added. The pH of the solution is adjusted to 5 with $HNO_3$. With stirring, the whole mixture is heated to 60° C. and maintained for twenty-four hours. The zeolite is separated from the solution by filtration and washed with distilled and deionized water three times, 48 L water each time. The zeolite is filtered, dried at 110° C. overnight and calcined at 550° C. for six hours in air. An excessive amount of salt can be employed to achieve high degree of exchange.

Solid Procedure

To conduct solid-state ion-exchange, a calculated amount of metal salt, such as $CuCl_2$ for $Cu^{2+}$ exchange, is mixed with dry $H^+$ form zeolite. The mixture is heated in $N_2$ to 550° C. at a rate of 0.5° C./min and maintained at 550° C. for ten hours. The amount of the salt is based on how much $H^+$ needs to be exchanged. After the calcination, the zeolite can be used directly or it can be washed with distilled and deionized water, calcined again at 500° C. for three hours before use.

Examples 1–3

Figure 2:
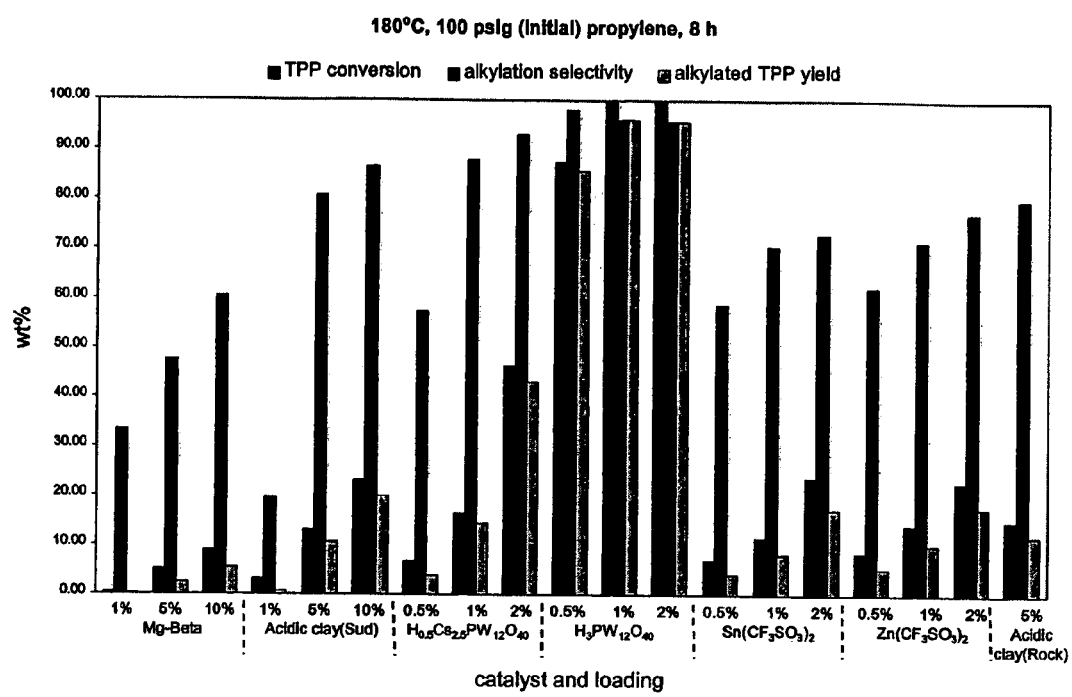
Figure 3:
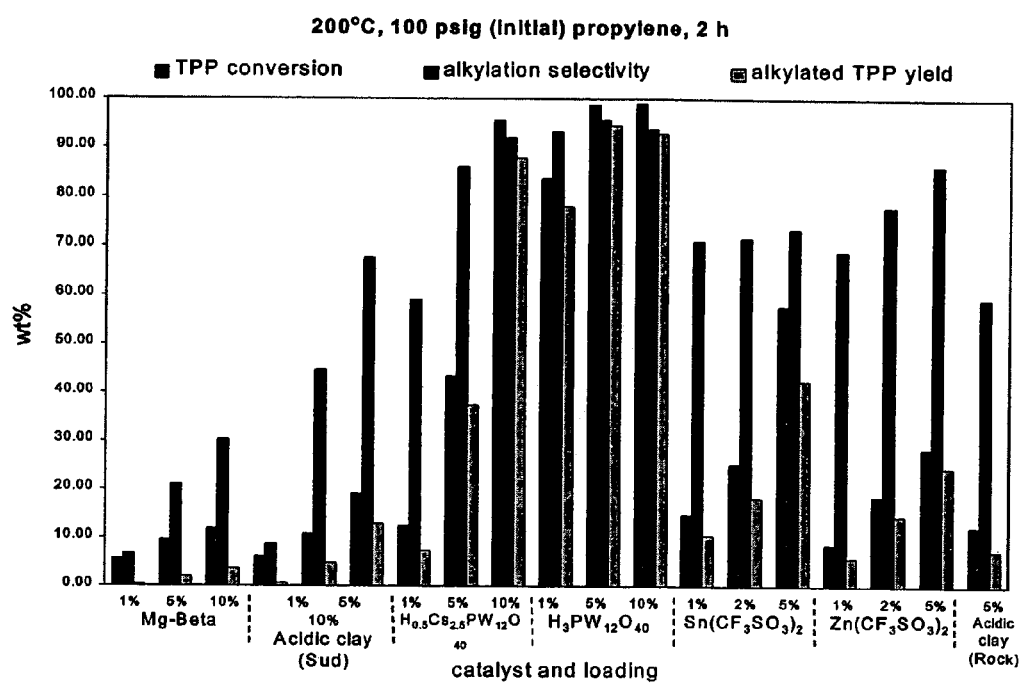

Three batches of TPP alkylation reactions were conducted in a high throughput batch reactor system and are shown in FIGS. 1 to 3.

Lewis acids SnCl4, ZnCl2, and EuCl3 showed different activity and selectivity to desired products.

Zeolites and metal exchanged zeolites also showed activity and selectivity toward desired products.

Examples 4–6

In a conventional autoclave reactor (200 ml) with magnetic stir, $H_3PW_{12}O_{40}$ and acidic clay, as a comparative run, were tested. The TPP loading was 40 g each run. Table 1 summarizes the reaction conditions and the results. Even though much more acidic clay and a much high temperature were used for the acidic clay (a comparative case), the conversion of TPP from the acidic clay was much lower than that obtained from the $H_3PW_{12}O_{40}$. Much higher selectivity was obtained with the $H_3PW_{12}O_{40}$.

TABLE 1

TPP alkylation in a Conventional Autoclave Reactor

|  | Reaction conditions | TPP conversion (wt %) | Alkylation selectivity (wt %) |
| --- | --- | --- | --- |
| 0.2 wt % $H_3PW_{12}O_{40}$ | 200° C., 8 h, 120 psig propylene (initial) | 50.5 | 99.8 |
| 0.4 wt % $H_3PW_{12}O_{40}$ | 200° C., 8 h, 120 psig propylene (initial) | 60.5 | 91.0 |
| 5 wt % Acidic clay (Comparative run) | 250° C., 8 h, 110 psig propylene (initial) | 20.7 | 64.1 |

Example 7

TPP Alkylation with 1-hexadecene

Figure 4:
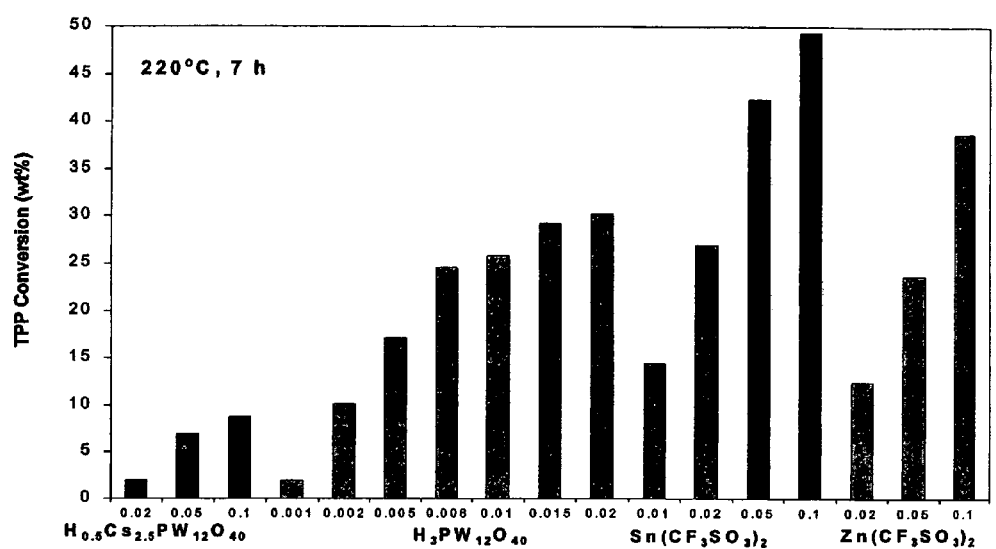

One batch of TPP alkylation with 1-hexadecene ($1\text{-}C_{16}^1$) was conducted in the high throughput reactor. Four catalysts, $H_{0.5}Cs_{2.5}PW_{12}O_{40}$, $H_3PW_{12}O_{40}$, $Sn(CF_3SO_3)_2$, and $Zn(CF_3SO_3)_2$, with different loading were tested. The reaction conditions were 220° C., 7h, TPP/$1\text{-}C_{16}^1$ (molar ratio)=1, 100 psig $N_2$(initial). For each test, 0.73 g of TPP and 0.5 g of $1\text{-}C_{16}^1$ were used. Catalyst amounts (gram) and TPP conversions (wt %) are shown in FIG. 4. Almost 100% of converted TPP formed alkylated products.

Example 8

TPP Alkylation with 1-hexene

Figure 5:
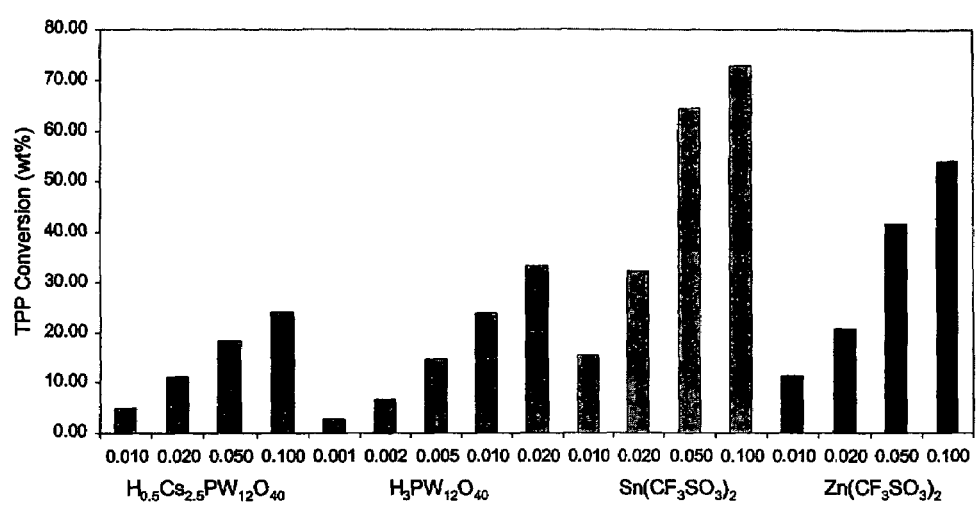

One batch of TPP alkylation with 1-hexene ($1\text{-}C_6^1$) was conducted in the high throughput reactor. Four catalysts, $H_{0.5}Cs_{2.5}PW_{12}O_{40}$, $H_3PW_{12}O_{40}$, $Sn(CF_3SO_3)_2$, and $Zn(CF_3SO_3)_2$, with different loading were tested. The reaction conditions were 200° C., 7h, TPP/$1\text{-}C_6^1$ (molar ratio)=0.5, 0 psig $N_2$(initial). For each test, 1.0 g of TPP and 0.52 g of $1\text{-}C_6^1$ were used. Catalyst amounts (gram) and TPP conversions (wt %) are shown in FIG. 5. Homogeneous liquid solutions were formed for all tests. Almost 100% of converted TPP formed alkylated products.

The invention claimed is:

1. A process for the alkylation of triphenylphosphate by reaction of triphenylphosphate with an olefin in the presence of an effective amount of a solid acid catalyst selected from the group consisting of at least one zeolite, a metal triflate, a non-aryl group-containing metal sulfonic acid and compatible mixtures of any such catalyst.

2. A process as claimed in claim 1 wherein the catalyst is a zeolite.

3. A process as claimed in claim 1 wherein a zeolite contains protons as a Bronsted acid catalyst.

4. A process as claimed in claim 1 wherein a zeolite contains exchanged metal ions.

5. A process as claimed in claim 1 wherein a zeolite contains extra framework Lewis acid sites.

6. A process as claimed in claim 1 wherein the catalyst is a metal triflate.

7. A process as claimed in claim 1 wherein the catalyst is a non-aryl group-containing metal sulfonic acid.

8. A process for the alkylation of triphenylphosphate by reaction of triphenylphosphate with an olefin in the presence of an effective amount of a solid acid catalyst, wherein said solid acid catalyst is a heteropolyacid or salt thereof.

* * * * *